(12) United States Patent
Takai

(10) Patent No.: US 6,334,682 B1
(45) Date of Patent: Jan. 1, 2002

(54) OPHTHALMOLOGY APPARATUS

(75) Inventor: Motoya Takai, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/604,162

(22) Filed: Jun. 27, 2000

(30) Foreign Application Priority Data

Jun. 29, 1999 (JP) .................................................. 11-183567

(51) Int. Cl.$^7$ .................................................. A61B 3/14
(52) U.S. Cl. .................................................. 351/206
(58) Field of Search .................................. 351/205, 206, 351/210, 211, 214, 216, 217, 218, 237, 233, 236, 243

(56) References Cited

U.S. PATENT DOCUMENTS 4,917,480 A * 4/1990 Kato et al. .................... 351/211

* cited by examiner

Primary Examiner—George Manuel
(74) Attorney, Agent, or Firm—Fitzpatrick, Cella, Harper & Scinto

(57) ABSTRACT

An ophthalmology apparatus has an illuminating system which illuminates an eye to be examined, an imaging system which takes images of the eye to be examined illuminated by the illuminating system, and a controller capable of controlling the imaging system so as to obtain the plurality of images sequentially while changing focusing states.

4 Claims, 3 Drawing Sheets

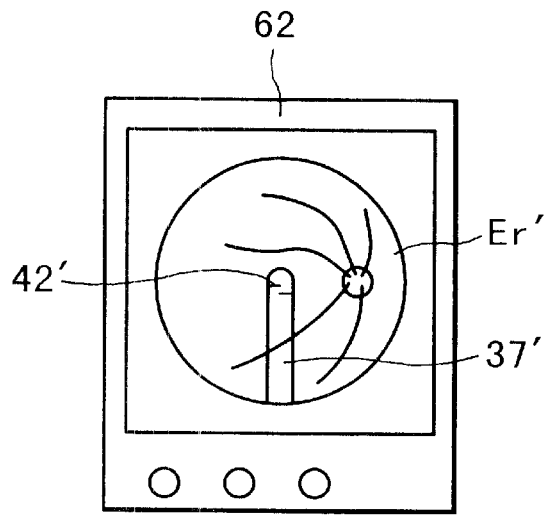
FIG. 2
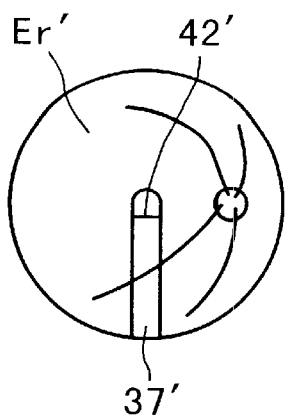 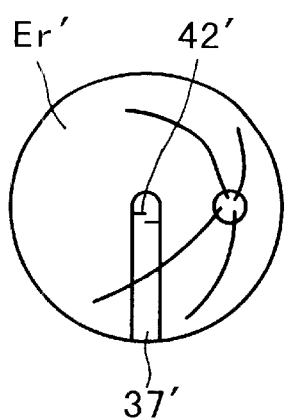 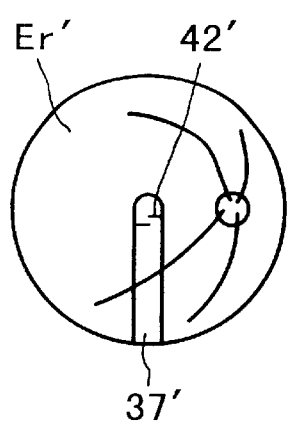
FIG. 3A   FIG. 3B   FIG. 3C

US 6,334,682 B1

OPHTHALMOLOGY APPARATUS

BACKGROUND OF THE INVENTION

1. Field of the Invention

The present invention relates to an ophthalmology apparatus, such as a retinal camera or the like, used in ophthalmic hospitals, in health screening, and so on.

2. Related Background Art

There are conventionally known, digital, retinal cameras for taking electronic images in low light amounts by use of a CCD camera or the like to record images of the eyeground and the like. FIG. 4 is a structural diagram to show the structure of a conventional retinal camera, in which light emitted from an observation light source 1 travels via lenses 2, 3, a ring stop 4, a lens 5, a bored mirror 6, an objective 7, etc. to illuminate the eyeground Er of an eye to be examined E. Reflected light from the eyeground travels through the objective 7 and a taking lens 8 and then is bent by a path changeover mirror 9 and a dichroic mirror 10 to travel via a field lens 11, a field stop 12, and an imaging lens 13 to be focused on an observation TV camera 14. A small mirror 15 is put into the optical path, whereby a split chart 17, illuminated by a split projection light source 16, is projected via an optical system 18 onto the eyeground Er.

Based on a projection image of this split chart 17, an operator moves the taking lens 8 along the optical path so as to align left and right bright lines with each other, thereby bringing the eye to be examined E into focus. After completion of focusing, the operator manipulates a fixation target moving switch, not illustrated, in order to photograph a predetermined portion of the eye to be examined E, and then moves an opening portion of liquid-crystal shutter 19 to guide the desired portion of the eye to be examined E into the field by a fixation target 20. Unless there is any defocus at this time, the operator depresses a photograph switch 21 to light a photograph light source 22 in the illumination optical system, thereby illuminating the eyeground Er. The reflected light from the eyeground Er is guided through the objective 7, the aperture of the bored mirror 6, the taking lens 8, a field lens 23, a field stop 24, and an imaging lens 25 to form an image on an image pickup device 26. The output of the image pickup device 26 is supplied through a controller 27 to an image recording device 28 to record a still image and to a television monitor 29 to display a dynamic picture.

In the above-stated example, however, since the target projected for focusing of the eye to be examined E is only one meridian of the eye to be examined E, there will exist in-focus and out-of-focus portions in a single image if the eye to be examined E suffers an ametropia such as astigmatism or the like. The human eye also has spherical aberrations which cause the existence of in-focus and out-of-focus portions. Therefore, the operator needs to adjust the focus position again before photography and these operations require some time and labor. Problems which are troublesome.

SUMMARY OF THE INVENTION

An object of the present invention is to solve the above-stated problem, thereby providing an ophthalmology apparatus capable of taking a plurality of images at different focus positions by a single photographing operation.

For accomplishing the above object, the present invention provides an ophthalmology apparatus comprising:

an illuminating system which illuminates an eye to be examined;

an imaging system which takes image of the eye to be examined illuminated by the illuminating system; and a controller capable of controlling the imaging system so as to obtain the plurality of images sequentially while changing focusing states.

BRIEF DESCRIPTION OF THE DRAWINGS

FIG. 2 is an explanatory diagram of a screen of the TV monitor;

FIGS. 3A, 3B, and 3C are explanatory diagrams of images of the image recording device.

DETAILED DESCRIPTION OF THE PREFERRED EMBODIMENTS

The present invention will be described hereinafter in detail, based on the embodiment illustrated in FIG. 1 to FIG. 3C.

Figure 1:
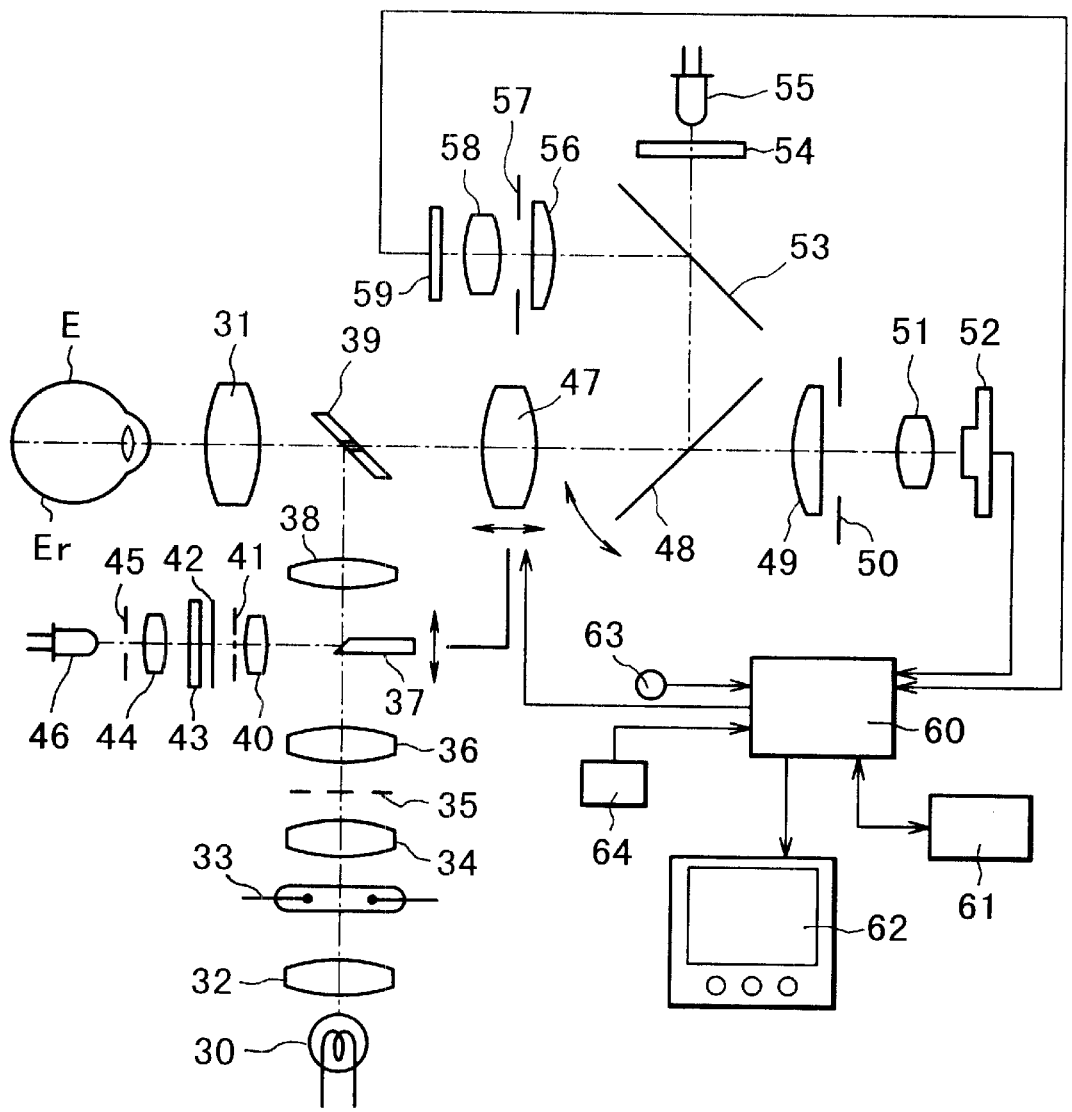
FIG. 1 is a side view of a retinal camera according to an embodiment of the present invention.
Figure 4:
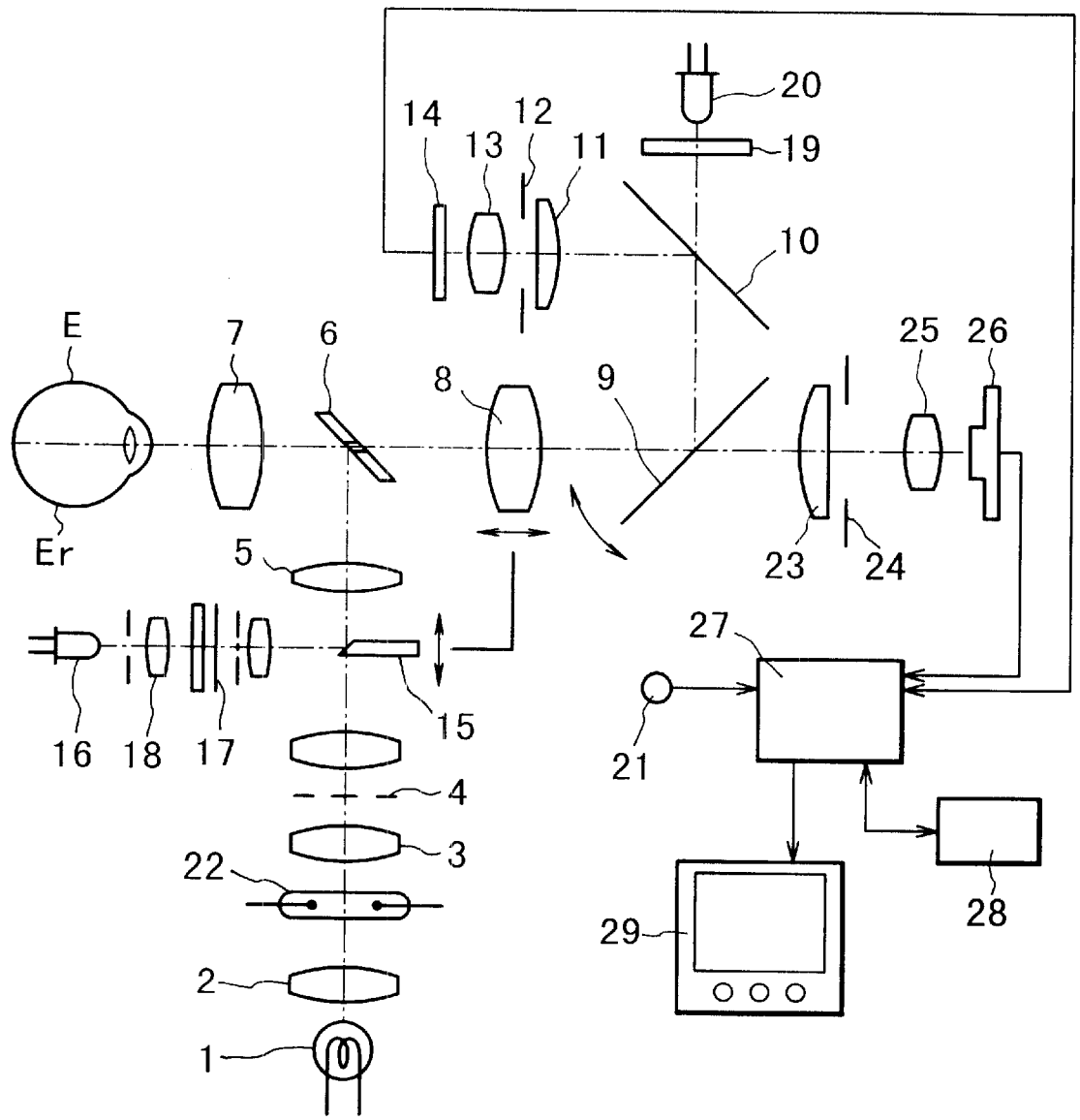
FIG. 4 is a side view of the conventional example.

FIG. 1 is a structural diagram of a digital, retinal camera according to the embodiment, in which a relay lens 32, a photograph light source 33, a relay lens 34, a ring stop 35, a relay lens 36, a small mirror 37 retractable from the optical path, a relay lens 38, and a bored mirror 39 having an aperture in the central part are arranged in the order named on the optical path from an observation light source 30 to an objective 31 opposed to the eye to be examined E. Arranged on the optical path along the direction of incidence to the small mirror 37 are a lens 40, a two-hole stop 41 approximately conjugate with the pupil position of the eye to be examined E with respect to the objective 31 and the relay lens 38, a split chart 42 approximately conjugate with the eyeground Er of the eye to be examined E with respect to the objective 31, the relay lens 38, and the lens 40, a split prism 43, a relay lens 44, a stop 45, and a split projection light source 46. These split projection optics are movable along the optical path of the illumination optical system, as indicated by arrows, together with the small mirror 37.

A taking lens 47, which is movable on the optical path in directions of arrows in association with movement of the small mirror 37 by a driving mechanism, is placed on the optical path behind the bored mirror 39. Further, a path changeover mirror 48, a field lens 49, a field stop 50, an imaging lens 51, and an image pickup device 52 such as the CCD or the like, are arranged in the stated order after the taking lens 47. Arranged on the optical path along the direction of reflection of the path changeover mirror 48 are a dichroic mirror 53, a liquid-crystal shutter 54 which has an opening portion and which presents the fixation target for the eye to be examined E, and an illumination light source 55 for illuminating this liquid-crystal shutter 54. A field lens 56, a field stop 57, an imaging lens 58, and a TV camera 59 for observation of the eye to be examined are arranged on the optical path along the direction of reflection of the dichroic mirror 53.

The image pickup device 52 and the TV camera 59 are connected to a controller 60. Further connected to the controller 60 are an image recording device 61, a TV monitor 62, an image pickup switch 63, a correction amount input device 64 such as a keyboard or the like, and the driving mechanism of the taking lens 47.

Light emitted from the observation light source 30 travels through the relay lenses 32, 34, the ring stop 35, and the relay lenses 36, 38 to be reflected by the bored mirror 39 to illuminate the eyeground Er of the eye to be examined E through the objective 31. Reflected light from the eyeground Er travels through the objective 31, the bored mirror 39, and the taking lens 47 to be bent by the path changeover mirror 48 and the dichroic mirror 53 and then the light travels through the field lens 56, the field stop 57, and the imaging lens 58 to form an image on the observation TV camera 59.

At this time the small mirror 37 is brought into the optical path and the split projection light source 46 is switched on. Light from this light source 46 travels through the stop 45, the relay lens 44, and the split prism 43 to illuminate the split chart 42. Then the light travels via the two-hole stop 41, relay lens 40, small mirror 37, relay lens 38, bored mirror 39, and objective 31 to be projected onto the eyeground Er of the eye to be examined E. This causes a small mirror image 37', together with an eyeground image Er', to be displayed on the screen of the TV monitor 62, as illustrated in FIG. 2, and split bright lines 42' from the split chart 42 are displayed in the upper part of the small mirror image.

Based on this picture, the operator moves the taking lens 47 along the optical path in synchronism with the small mirror 37 by manipulating an unrepresented dial or the like so as to align the split bright lines 42' with each other, thereby bringing the eye to be examined E into focus. After completion of focusing, the operator enters a correction amount before and after the focus position through the correction amount input switch 64. In order to photograph a desired portion of the eye to be examined E, the operator then manipulates an unrepresented fixation target moving switch to move the opening portion of the liquid-crystal shutter 54 illuminated by the light source 55, thereby guiding the desired portion of the eye to be examined E into the field. On that occasion, the operator checks whether there exists defocus. If there is some defocus, the operator will again perform the focusing operation.

After confirming the absence of defocus, the operator depresses the photograph switch 63 to switch the photograph light source 33 on. Light from the photograph light source 33 travels through the optical path similar to the observation optical path, to illuminate the eyeground Er of the eye to be examined E. Reflected light from the eyeground Er travels through the objective 31, the aperture of the bored mirror 39, the taking lens 47, the field lens 49, the field stop 50, and the imaging lens 51 to form an image on the image pickup device 52. A digital image signal of the eyeground image Er' obtained thereby is recorded as a still image in the image recording device 61.

FIGS. 3A to 3C show images recorded in the image recording device 61. With the reference being the image of FIG. 3A of the aligned split bright lines 42', the controller 60 performs such control as to obtain a plurality of images of the same eye to be examined E at the positions of FIGS. 3B and 3C sequentially while moving the taking lens 47 by the driving mechanism, for example, in accordance with the correction amounts of ±0.5 diopter entered through the correction amount input switch 64. During this period of sequential photography, the small mirror 37 and path changeover mirror 48 are each off the optical path.

The present embodiment is arranged to carry out the photography of three consecutive photographs with entry of the correction amount before and after the focus position, but the apparatus may also be modified to be able to perform an arbitrary number of photographing operations at any focus position. The present embodiment is arranged to give the entry of correction amount after the focusing operation, but the entry of correction amount may be made anytime before photography. Further, the correction amount may also be preliminarily stored in a memory, without entering it as occasion demands.

Further, the apparatus may also be arranged to receive input of spherical and astigmatic diopters obtained by a measuring device such as a refractor or the like and take consecutive photographs at the strongest principal meridian, at the weakest principal meridian, and at an intermediate or another focus position of the eye to be examined E. In this case, the measurement data from the other ophthalmology instrument is entered into the apparatus through the keyboard or the like by the operator, or an interface is prepared for the entry by communication.

Since the ophthalmology apparatus described above is constructed to take a plurality of images at different focus positions by a single photographing operation, it does not have to perform another photographing operation even if the eye to be examined suffers an ametropia, such as astigmatism or the like, or otherwise has a spherical aberation; therefore, it permits the photography with good efficiency.

What is claimed is:

1. An ophthalmology apparatus for taking images of an eyeground comprising:

an illuminating system which illuminates an eyeground of an eye to be examined;

an imaging system which takes a plurality of images of the eyeground illuminated by said illuminating system; and a controller which controls said imaging system so as to obtain the plurality of images of the same eyeground sequentially while changing focusing states of the imaging system.

2. An apparatus according to claim 1, wherein said imaging system comprises a lens movable along an optical path, and an image pickup device.

3. An apparatus according to claim 1, further comprising an imaging switch connected to said controller, for permitting an operator to give a direction of image-taking.

4. An apparatus according to claim 1, further comprising an input device connected to said controller for setting the focusing state of said imaging system.

* * * * *

UNITED STATES PATENT AND TRADEMARK OFFICE
CERTIFICATE OF CORRECTION

PATENT NO.   : 6,334,682 B1
DATED        : January 1, 2002
INVENTOR(S)  : Motoya Takai It is certified that error appears in the above-identified patent and that said Letters Patent is hereby corrected as shown below:

<u>Column 1,</u>
Line 56, "labor. Problems" should read -- labor, problems --.

Signed and Sealed this

Thirtieth Day of July, 2002

Attest:

Attesting Officer

JAMES E. ROGAN
*Director of the United States Patent and Trademark Office*